United States Patent [19]

Elischer et al.

[11] Patent Number: 4,535,160

[45] Date of Patent: Aug. 13, 1985

[54] PROCESS FOR OBTAINING SOLID CYANURIC CHLORIDE IN FINELY DIVIDED FORM

[75] Inventors: Stefan Elischer, Münchsmünster; Hans-Günther Höbel, Aiglsbach; Robert Merkt; Fritz Wagner, both of Münchsmünster, all of Fed. Rep. of Germany

[73] Assignee: SKW Trostberg Aktiengesellschaft, Trostberg, Fed. Rep. of Germany

[21] Appl. No.: 636,335

[22] Filed: Jul. 31, 1984

[30] Foreign Application Priority Data

Oct. 11, 1983 [DE] Fed. Rep. of Germany ....... 3336993

[51] Int. Cl.$^3$ ............................................. C07D 251/28
[52] U.S. Cl. ...................................... 544/191; 544/190
[58] Field of Search ................................ 544/190, 191

[56] References Cited

U.S. PATENT DOCUMENTS

| | | | |
|---|---|---|---|
| 2,734,058 | 2/1956 | Schulz et al. | 544/190 |
| 2,742,977 | 4/1956 | Williams et al. | 544/190 |
| 2,753,346 | 7/1956 | Huemer | 544/190 |
| 3,409,619 | 11/1968 | Kosel | 544/190 |
| 3,539,565 | 11/1970 | Evers et al. | 544/190 |

*Primary Examiner*—John M. Ford
*Attorney, Agent, or Firm*—Felfe & Lynch

[57] ABSTRACT

The present invention provides a process for obtaining solid cyanuric chloride from the cyanuric chloride vapor obtained by trimerizing cyanogen chloride by separating out in a separation chamber, wherein cyanuric chloride vapor and cold air are introduced into the separation chamber through obliquely upwardly directed inlets in such a manner that an intensive mixing up of the cyanuric chloride vapor with the cold air takes place after emergence from the inlet pipes, the cyanuric chloride-free waste gases are withdrawn from the upper part of the separation chamber and the solid cyanuric chloride is removed from the lower part of the separation chamber.

12 Claims, 1 Drawing Figure

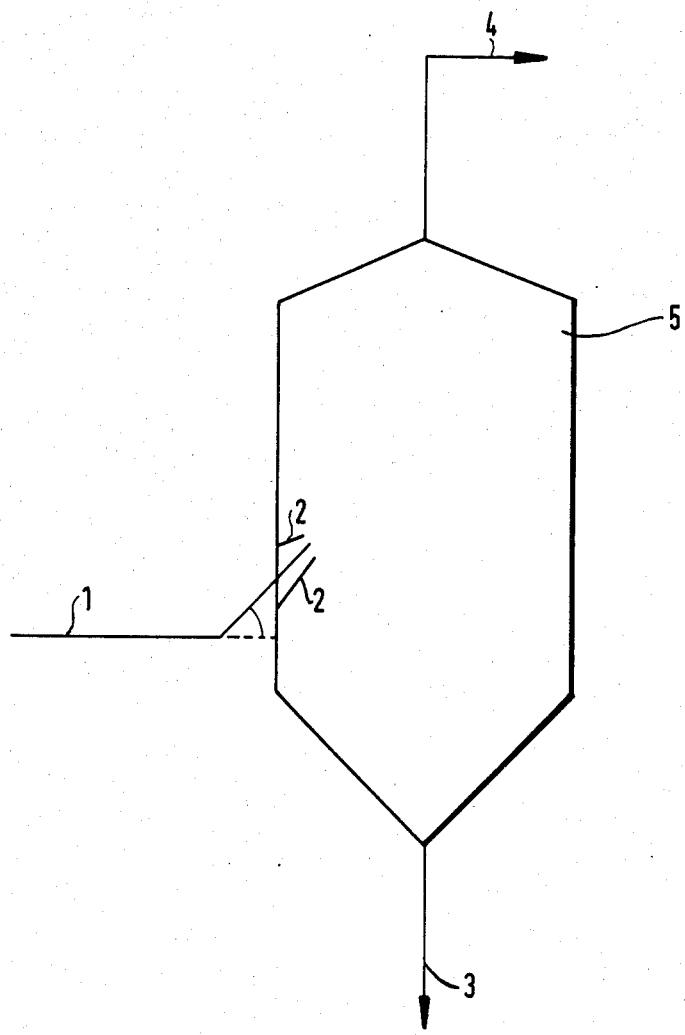

PROCESS FOR OBTAINING SOLID CYANURIC CHLORIDE IN FINELY DIVIDED FORM

The present invention is concerned with a process for obtaining solid cyanuric chloride in finely divided form.

Cyanuric chloride, which is of considerable technical importance as an intermediate product for the production of dyestuffs, plant protection agents and pharmaceuticals, as well as of textile and rubber adjuvants, is obtained, after the catalytic trimerisation of cyanogen chloride, in gaseous form, together with unreacted cyanogen chloride and chlorine. This gas mixture is usually passed into separation chambers and the cyanuric chloride is deposited out on the cooled walls thereof. It is a disadvantage of this kind of desublimation that the cyanuric chloride deposits in the form of coarse crystals on the walls and removal devices and thus has an adverse influence on heat transmission. Regular knocking off of the crystals from the walls admittedly results in a brief improvement of the heat transmission but, because of the increasing mechanical damaging and the noise, this method is in no way satisfactory, quite apart from the poor quality of the product obtained in this way.

According to Federal Republic of Germany Patent Specification No. 12 66 308, the attempt has been made to overcome this problem in that cyanuric chloride, together with a readily evaporating inert cooling liquid, for example chloroform, is sprayed. In this way, a finely divided cyanuric chloride is admittedly obtained but the recovery of the cooling liquid is quite laborious. Furthermore, blockages of the nozzle can occur very easily.

Finally, Federal Republic of Germany Patent Specification Nos. 28 43 381 and 28 43 382 describe processes for obtaining liquid or solid cyanuric chloride according to which the reaction mixture obtained after the trimerisation of cyanogen chloride is passed in to an apparatus combination comprising a removal column and condenser and, by temperature regulation and admixture of inert gas (for the prevention of total condensation) at the outlet of the condenser, the cyanuric chloride is partly condensed in the column, whereas the gaseous part, which emerges at the column head, is desublimated in conventional separation chambers. In the case of this method, a disadvantage is the laborious apparatus combination which gives rise to high investment and operational costs.

Therefore, it is an object of the present invention to provide a process for obtaining solid cyanuric chloride which does not possess the described disadvantages of the prior art and, without great technical expense, makes a cyanuric chloride available which, with regard to particle distribution and purity of the product, provides satisfactory results.

Thus, according to the present invention, there is provided a process for obtaining solid cyanuric chloride from the cyanuric chloride vapour obtained by trimerising cyanogen chloride by separating out in a separation chamber, wherein cyanuric chloride vapour and cold air are introduced into the separation chamber through obliquely upwardly directed inlets in such a manner that an intensive mixing up of the cyanuric chloride vapour with the cold air takes place after emergence from the inlet pipes, the cyanuric chloride-free waste gases are withdrawn from the upper part of the separation chamber and the solid cyanuric chloride is removed from the lower part of the separation chamber.

According to this process, there is, surprisingly, obtained an extremely finely divided and simultaneously very pure cyanuric chloride, laborious apparatus for additional purification steps thereby becoming unnecessary.

According to the present invention, the cyanuric chloride vapour, which can still contain numerous impurities, is passed, after emergence from the trimerisation reactor, into the separation chamber. Since a gas lowering the partial pressure is not added, the pipe between the reactor and the separation chamber must be heat-insulated in order to prevent a premature condensation of the cyanuric chloride, which can lead to undesired blockages.

Before entry into the separation chamber, the gaseous reaction mixture preferably has a temperature of from 250 to 300° C. in order that a good chilling effect by the cold air is ensured. The hot cyanuric chloride vapours are blown in through an obliquely upwardly directed inlet pipe preferably into the lower part of the separation chamber, together with separately introduced cold air, the cold air preferably having a temperature of from 0° to 60° C. and especially of from 10° to 25° C. The inlet should have an angle to the horizontal of 10° to 80° and preferably of 30° to 50° in order that it results in a good air circulation within the separation chamber, which also ensures a good heat exchange. In this way, the undesired separation of coarse crystals on the walls and the removal devices is prevented and, furthermore, the separation process is substantially accelerated.

For the achievement of the effect according to the present invention, it is advantageous to admix the cyanuric chloride vapour in the separators with cold air in amounts of 20 to 150 kg. and preferably 50 to 75 kg. per 100 kg. cyanuric chloride. It has proved to be especially advantageous to provide several and especially four or more cold air nozzles which are arranged obliquely to the cyanuric chloride inlet and tangentially to the cyanuric chloride stream. These rapidly emerging cold air streams have an ejector action and entrain ambient air proportionally to their mass and the square of their velocity. The sucked in amount of ambient air amounts, in general, to the $10^3$ fold amount of the blown in amount of ejector air. The intensive mixing up of these large amounts of air leads within seconds to a chilling effect which allows the cyanuric chloride to condense out in an especially finely divided form. The cyanuric chloride then separates out very quickly in the air stream and is thereby obtained in an especially finely divided form (preferably at most 3 to 4% of the particles have a particle size of >60 μm.). The product is removed from the lower part of the separation chamber, whereas the practically cyanuric chloride-free waste gases are withdrawn from the upper part of the chamber.

Besides this fine state of division, the cyanuric chloride produced according to the process of the present invention also already has a very high degree of purity (cyanuric chloride content>99.5%, hydroxytriazine<0.5%, polytriazines<0.1%) and can, therefore, in most cases, be further worked up directly without further purification operations. With the cyanuric chloride obtained by the process according to the present invention, there is obtained, for example, atrazine in a yield of 99%, which was not possible directly with the cyanuric chloride obtained according to the prior art. Furthermore, the extremely fine state of division of the cyanuric chloride leads to a very considerable increase of the reactivity. The reaction time for the production of atrazine is considerably reduced.

The present invention will now be described in more detail with reference to the accompanying drawing and to the following Examples.

BRIEF DESCRIPTION OF THE DRAWING

The drawing shows schematically apparatus which can be used according to the present invention for obtaining solid cyanuric chloride from a reaction gas mixture obtained by the trimerisation of cyanogen chloride.

DESCRIPTION OF THE INVENTION

Referring to the drawing, cyanogen chloride vapor is introduced through pipe (1) into the lower part of a separation chamber (5). On the inlet into the chamber (5), the pipe (1) is directed obliquely upwardly. Cold air is introduced through nozzles (2). After desublimation, solid material is removed via pipe (3), whereas waste gases are withdrawn via pipe (4) on the upper part of the separation chamber (5).

EXAMPLE 1

After emerging from a trimerisation reactor, the cyanuric chloride vapour thereby obtained, which still contains impurities, for example cyanogen chloride or chlorine, is introduced through pipe (1) in an amount of 250 kg./hour into the lower part of the separation chamber (5), the pipe (1) thereby having an angle of 45° to the horizontal. At the same time, 135 kg./hour of cold air with a temperature of 25° C. are passed through several nozzles (2) into the separation chamber (5) and thereby brings about the separation of cyanuric chloride. Whereas the cold air, together with residual gases, is withdrawn from the upper part of the separation chamber, the finely divided solid cyanuric chloride collects on the bottom of the separation chamber, from where it is removed. The product obtained has the following particle distribution:

>125 μm.—0%
125–63 μm.—1.6%
40–63 μm.—9.5%
<40 μm.—88.9%

EXAMPLE 2

In the manner described in Example 1, 250 kg. cyanuric chloride vapour are passed hourly into the separation chamber, together with 135 kg. of cold air with a temperature of 10° C., and cyanuric chloride is separated out. The cyanuric chloride obtained has the following particle distribution:

>60 μm.—3%
40–60 μm.—30%
<40 μm.—67%

We claim:

1. A process for recovering solid cyanuric chloride from the cyanuric chloride vapour obtained by trimerizing cyanogen chloride comprising the steps of separately introducing the cyanuric chloride vapour and cold air into a separation chamber through obliquely upwardly directed inlets in the chamber, in such a manner that an intensive mixing up of the cyanuric chloride vapour with the cold air takes place after emergence from the inlet pipes to precipitate solid cyanuric chloride from the vapor, withdrawing cyanuric chloride-free waste gases from the upper part of the separation chamber and removing the precipitated solid cyanuric chloride from the lower part of the separation chamber.

2. Process according to claim 1, wherein the cyanuric chloride vapour and the cold air are introduced into the lower part of the separation chamber.

3. Process according to claim 1, wherein the angle of the cyanuric chloride inlet pipe to the horizontal is 10° to 80°.

4. Process according to claim 3, wherein the angle of the cyanuric chloride pipe to the horizontal is 30° to 50°.

5. Process according to claim 1 wherein the cold air has a temperature of from 0° to 60° C.

6. Process according to claim 5, wherein the cold air has a temperature of from 10° to 25° C.

7. Process according to claim 1 wherein cold air is added to the cyanuric chloride in an amount of from 20 to 150 kg. per 100 kg. of cyanuric chloride.

8. Process according to claim 7, wherein cold air is added to the cyanuric chloride in an amount of from 50 to 75 kg. per 100 kg. of cyanuric chloride.

9. Process according to claim 1 wherein cold air is admixed with the cyanuric chloride through several nozzles arranged obliquely to the cyanuric chloride inlet and tangentially to the cyanuric chloride stream.

10. A process for recovering solid cyanuric chloride from cyanuric chloride containing vapor obtained by trimerizing cyanogen chloride, comprising the steps of
mixing the cyanuric chloride vapor with cold air having a temperature of 0° 14 60° C. in an amount of 20 to 150 kg cold air per 100 kg cyanuric chloride, to precipitate solid cyanuric chloride from the vapor; and
separating the solid cyanuric chloride from the vapor.

11. A process for recovering solid cyanuric chloride from cyanuric chloride vapor comprising the steps of
separately introducing and thereafter mixing cyanuric chloride vapor and cold air having a temperature of 0° to 60° C., in a separation chamber in ratio of about 20 to 150 kg air to 100 kg cyanuric chloride vapor, to precipitate solid cyanuric chloride from the vapor-air mixture and
separating the solid cyanuric chloride from the mixture.

12. The process of claim 11 wherein the cyanuric chloride is introduced through inlets to the chamber, the inlets being at an angle of 10° to 80° to the horizontal.

* * * * *

UNITED STATES PATENT AND TRADEMARK OFFICE
CERTIFICATE OF CORRECTION

PATENT NO. : 4,535,160
DATED : August 13, 1985
INVENTOR(S) : Stefan Elischer et al It is certified that error appears in the above-identified patent and that said Letters Patent are hereby corrected as shown below:

Claim 10, line 5, "0°1460°C" should be -- 0-60°C --.

Signed and Sealed this

First Day of April 1986

[SEAL]

Attest:

DONALD J. QUIGG

Attesting Officer

Commissioner of Patents and Trademarks